US012780787B2

(12) United States Patent
Liu et al.

(10) Patent No.: US 12,780,787 B2
(45) Date of Patent: Nov. 3, 2026

(54) AMIDE COMPOUND CONTAINING SUBSTITUTED ACETOPHENONE STRUCTURAL FRAGMENTS AND PREPARATION METHOD AND APPLICATION THEREOF

(71) Applicants: SHENYANG SINOCHEM AGROCHEMICALS R&D CO., LTD., Shenyang (CN); JIANGSU YANGNONG CHEMICAL CO., LTD., Yangzhou (CN)

(72) Inventors: Pengfei Liu, Shenyang (CN); Jinbo Zhang, Shenyang (CN); Jie Lan, Shenyang (CN); Yanming Ye, Shenyang (CN); Zhonggang Shan, Shenyang (CN); Yumeng Liu, Shenyang (CN); Aiying Guan, Shenyang (CN)

(73) Assignees: SHENYANG SINOCHEM AGROCHEMICALS R&D CO., LTD., Shenyang (CN); JIANGSU YANGNONG CHEMICAL CO., LTD., Yangzhou (CN)

( * ) Notice: Subject to any disclaimer, the term of this patent is extended or adjusted under 35 U.S.C. 154(b) by 695 days.

(21) Appl. No.: 17/755,480

(22) PCT Filed: Oct. 21, 2020

(86) PCT No.: PCT/CN2020/122394
§ 371 (c)(1),
(2) Date: Apr. 29, 2022

(87) PCT Pub. No.: WO2021/082997
PCT Pub. Date: May 6, 2021

(65) Prior Publication Data

US 2023/0167062 A1 Jun. 1, 2023

(30) Foreign Application Priority Data

Oct. 29, 2019 (CN) ......................... 201911038088.5

(51) Int. Cl.
*C07D 213/82* (2006.01)
*C07D 231/12* (2006.01)
*C07D 231/16* (2006.01)

(52) U.S. Cl.
CPC ......... *C07D 213/82* (2013.01); *C07D 231/12* (2013.01); *C07D 231/16* (2013.01)

(58) Field of Classification Search
None
See application file for complete search history.

(56) References Cited

U.S. PATENT DOCUMENTS

2010/0222337 A1* 9/2010 Nakamura ........... C07D 405/12 514/357
2010/0261735 A1* 10/2010 Nakamura ........... C07D 231/16 514/346

FOREIGN PATENT DOCUMENTS

| | | | | |
|---|---|---|---|---|
| CN | 101001528 A | * 7/2007 | ............. | A01N 37/20 |
| CN | 101330831 A | 12/2008 | | |
| CN | 100567286 C | * 12/2009 | ............. | A01N 37/20 |
| JP | 2007210924 A | 8/2007 | | |
| WO | 2006016708 A1 | 2/2006 | | |
| WO | 2007069777 A2 | 6/2007 | | |
| WO | 2011061205 A1 | 5/2011 | | |
| WO | 2014184235 A1 | 11/2014 | | |
| WO | 2015197530 A2 | 12/2015 | | |
| WO | 2016142918 A1 | 9/2016 | | |
| WO | 2019124537 A1 | 6/2019 | | |
| WO | 2019124538 A1 | 6/2019 | | |

OTHER PUBLICATIONS

CN101001528A google machine english translation accessed Oct. 19, 2024, pub. 2007.*
CN100567286C google machine english translation accessed Oct. 19, 2024, pub. 2009.*
Cambridge Medchem bioisosteres (http://web.archive.org/web/20130113020012/https://www.cambridgemedchemconsulting.com/resources/bioisosteres/) no pagination. (Year: 2013).*
Patani, et. al. Chem. Rev. 1996, 96, 3147-3176 (Year: 1996).*
Tice, Colin M. et al.; "Synthesis and SAR of -Acylaminoketone Ligands for Control of Gene Expression"; Bioorganic&Medicinal Chemistry Letters, vol. 13, No. 3, 2003, pp. 475-478.

(Continued)

*Primary Examiner* — Erin E Hirt
(74) *Attorney, Agent, or Firm* — NKL Law; Allen Xue

(57) ABSTRACT

The present invention discloses an amide compound containing substituted acetophenone structural fragments, having a structure shown by general formula I:

I

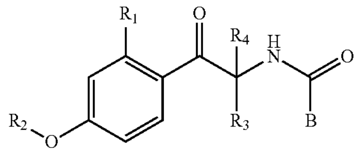

The definitions of substituents in the formula are shown in the description. The compound of the present invention has broad-spectrum fungal activity, and has excellent control effects on cucumber downy mildew, wheat powdery mildew, corn rust, cucumber anthracnose, cucumber botrytis and tomato botrytis.

5 Claims, No Drawings

(56) References Cited

OTHER PUBLICATIONS

Zaragoza, Florencio et al.; "Short and Safe Synthesis of Ethyl 3-(Trifluoromethyl) Pyrazine-2-Carboxylate"; Organic Process Research & Development; 2017, vol. 21, No. 3, pp. 448-450.
Hu, Aixi et al.; "Bromination of alkylaryl ketone with cupric bromide"; Chinese Journal of Medicinal Chemistry; vol. 12, No. 6, Dec. 2002; pp. 340-343.
Zhang, Shukang; "Technology research about the Synthesis of Succinate Dehydrogenase Inhibitor Fungicide Isofetamid"; Wuhan Institute of Technology( A Thesis submitted for the degree of Master), 2016.
Peng, Jiu-He et al.; "Chemoselective Reduction of 21-Azidocorticosteroids to Primary 21-Primary Aminocorticosteroids"; Chemical journal of chinese universities, vol. 25, No. 5, May 2004, pp. 866-869.

* cited by examiner

AMIDE COMPOUND CONTAINING SUBSTITUTED ACETOPHENONE STRUCTURAL FRAGMENTS AND PREPARATION METHOD AND APPLICATION THEREOF

TECHNICAL FIELD

The present invention belongs to the field of agricultural sterilization, and in particular relates to a novel amide compound containing substituted acetophenone structural fragments and a preparation method and application thereof.

BACKGROUND

Patent WO2007069777 discloses the amide compounds CK1 (patent number I-20) and CK2 (patent number I-84) shown by the following general formulas for application of prevention and treatment of fungal diseases such as wheat powdery mildew, cucumber powdery mildew, rice blast, kidney bean stem rot and wheat glume blotch.

CK1

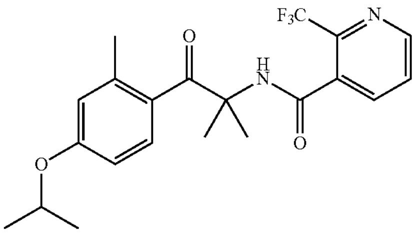

CK2

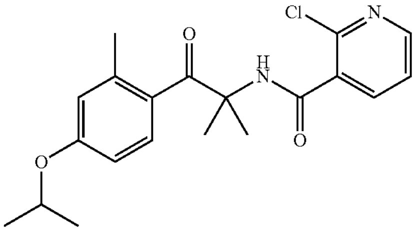

Patent JP 2007210924 discloses the amide compounds CK3 (patent number I-6) and CK4 (patent number I-183) represented by the following general formulas for application of prevention and treatment of fungal diseases such as wheat powdery mildew, cucumber powdery mildew, rice blast, kidney bean stem rot, kidney bean Sclerotinia sclerotiorum and wheat blight.

CK3

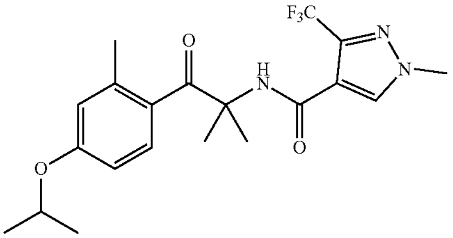

-continued

CK4

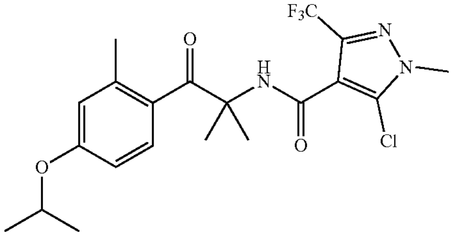

However, there is no report on the amide compound having structure shown in the general formula I in the present invention as a compound for agricultural sterilization.

SUMMARY

The purpose of the present invention is to provide an amide compound containing substituted acetophenone structural fragments that can control various germs, which is used in preparation of drugs for preventing and treating germs in agriculture or other fields.

To achieve the above purpose, the technical solution of the present invention is as follows:

The present invention provides an amide compound containing substituted acetophenone structural fragments, and the amide compound containing substituted acetophenone structural fragments is a compound shown by general formula I.

I

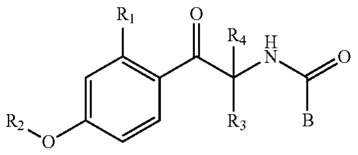

In the formula:

$R_1$ is selected from hydrogen, halogen, $C_1$-$C_{12}$ alkyl, halogenated $C_1$-$C_{12}$ alkyl, $C_1$-$C_{12}$ alkoxy or halogenated $C_1$-$C_{12}$ alkoxy;

$R_2$ is selected from hydrogen, $C_1$-$C_{12}$ alkyl, halogenated $C_1$-$C_{12}$ alkyl, $C_3$-$C_{12}$ cycloalkyl, $C_2$-$C_{12}$ alkenyl, $C_2$-$C_{12}$ alkynyl, $C_1$-$C_{12}$ alkoxy $C_1$-$C_{12}$ alkyl, halogenated $C_1$-$C_{12}$ alkoxy $C_1$-$C_{12}$ alkyl, $C_1$-$C_{12}$ alkylthio $C_1$-$C_{12}$ alkyl, halogenated $C_1$-$C_{12}$ alkylthio $C_1$-$C_{12}$ alkyl, $C_4$-$C_{12}$ cycloalkylalkyl or halogenated $C_4$-$C_{12}$ cycloalkylalkyl;

$R_3$ is selected from hydrogen, $C_1$-$C_{12}$ alkyl, halogenated $C_1$-$C_{12}$ alkyl, $C_1$-$C_{12}$ alkoxy, halogenated $C_1$-$C_{12}$ alkoxy, $C_3$-$C_{12}$ cycloalkyl, $C_1$-$C_{12}$ alkylthio, halogenated $C_1$-$C_{12}$ alkylthio, $C_1$-$C_{12}$ alkoxy $C_1$-$C_{12}$ alkyl, halogenated $C_1$-$C_{12}$ alkoxy $C_1$-$C_{12}$ alkyl, $C_1$-$C_{12}$ alkylthio $C_1$-$C_{12}$ alkyl or halogenated $C_1$-$C_{12}$ alkylthio $C_1$-$C_{12}$ alkyl;

$R_4$ is selected from $C_1$-$C_{12}$ alkyl, halogenated $C_1$-$C_{12}$ alkyl, $C_1$-$C_{12}$ alkoxy, halogenated $C_1$-$C_{12}$ alkoxy, $C_3$-$C_{12}$ cycloalkyl, $C_1$-$C_{12}$ alkylthio, halogenated $C_1$-$C_{12}$ alkylthio, $C_1$-$C_{12}$ alkoxy $C_1$-$C_{12}$ alkyl, halogenated $C_1$-$C_{12}$ alkoxy $C_1$-$C_{12}$ alkyl, $C_1$-$C_{12}$ alkylthio $C_1$-$C_{12}$ alkyl or halogenated $C_1$-$C_{12}$ alkylthio $C_1$-$C_{12}$ alkyl;

B is selected from pyridin-3-yl, 2-difluoromethylpyridin-3-yl, 1-methyl-3-trifluoromethyl-5-fluoro-pyrazol-4-yl, 1-ethyl-3-trifluoromethyl-5-fluoro-pyrazol-4-yl, 1-methyl-3-trifluoromethyl-5-methylthio-pyrazol-4-yl, 1-ethyl-3-trifluoromethyl-5-methylthio-pyrazol-4-yl, 1-methyl-3-trifluoromethyl-5-methylsulfonyl-pyrazol-4-yl, 1-ethyl-3-trifluoromethyl-5-methylsulfonyl-pyrazol-4-yl, 1-methyl-3-methyl-pyrazol-5-yl, 1-ethyl-3-methyl-pyrazol-5-yl, 1-methyl-5-methylpyrazol-3-yl or 1-ethyl-5-methylpyrazol-3-yl, and halogen-substituted isothiazolyl; or pyrazinyl, pyrimidinyl, 4-substituted 2-hydroxythiazol-5-yl, 5-substituted 1-methyl-3-difluoromethylpyrazol-4-yl and 5-substituted 1-ethyl-3-difluoromethylpyrazol-4-yl substituted by 1-2 identical or different following groups; and the following groups are hydrogen, methyl, difluoromethyl, trifluoromethyl, hydroxyl, methoxy, thiol, methylthio, methylsulfonyl or halogen;

In the amide compound containing substituted acetophenone structural fragments of the present invention, a preferred compound comprises: in the general formula I shown, $R_1$ is selected from hydrogen, halogen or $C_1$-$C_8$ alkyl;

$R_2$ is selected from hydrogen, $C_1$-$C_8$ alkyl, $C_3$-$C_8$ cycloalkyl or halogenated $C_1$-$C_8$ alkyl;

$R_3$ is selected from hydrogen, $C_1$-$C_8$ alkyl or halogenated $C_1$-$C_8$ alkyl;

$R_4$ is selected from $C_1$-$C_8$ alkyl or halogenated $C_1$-$C_8$ alkyl;

B is selected from any one of the following $B_1$-$B_{30}$;

$B_1$

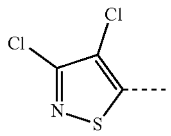

$B_2$

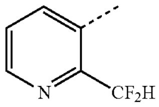

$B_3$

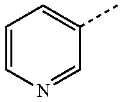

$B_4$

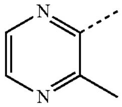

$B_5$

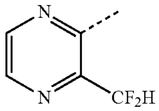

$B_6$

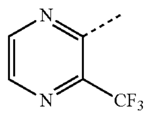

$B_7$

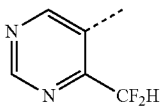

-continued $B_8$

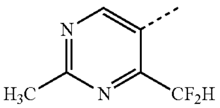

$B_9$

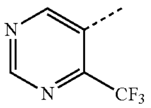

$B_{10}$

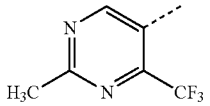

$B_{11}$

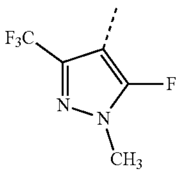

$B_{12}$

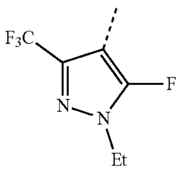

$B_{13}$

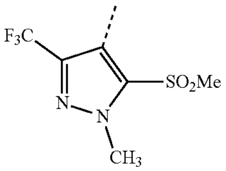

$B_{14}$

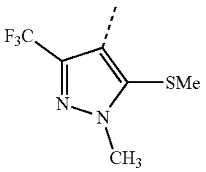

$B_{15}$

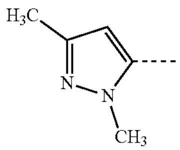

$B_{16}$

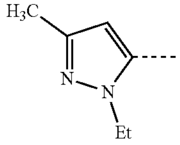

$B_{17}$

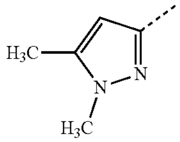

-continued $B_{18}$

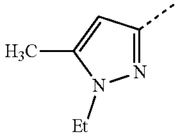

$B_{19}$

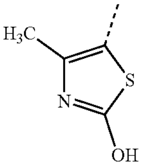

$B_{20}$

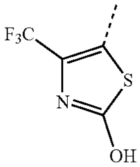

$B_{21}$

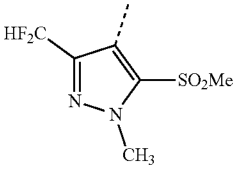

$B_{22}$

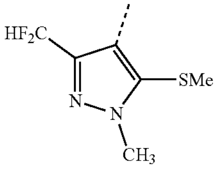

$B_{23}$

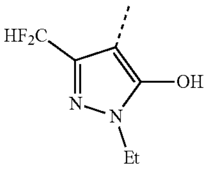

$B_{24}$

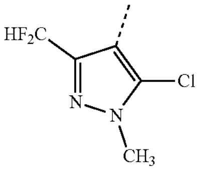

$B_{25}$

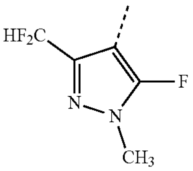

$B_{26}$

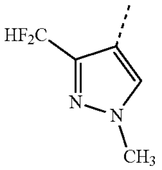

-continued $B_{27}$

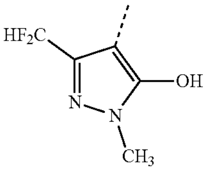

$B_{28}$

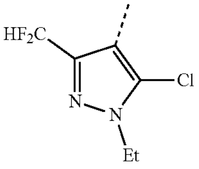

$B_{29}$

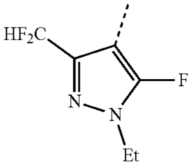

$B_{30}$

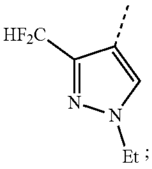

;

In the amide compound containing substituted acetophenone structural fragments of the present invention, a further preferred compound comprises: in the general formula I shown, $R_1$ is selected from hydrogen, halogen or $C_1$-$C_4$ alkyl;

$R_2$ is selected from hydrogen, $C_1$-$C_4$ alkyl, $C_3$-$C_6$ cycloalkyl or halogenated $C_1$-$C_4$ alkyl;

$R_3$ is selected from hydrogen, $C_1$-$C_4$ alkyl or halogenated $C_1$-$C_4$ alkyl;

$R_4$ is selected from $C_1$-$C_4$ alkyl or halogenated $C_1$-$C_4$ alkyl;

B is selected from any one of the following $B_1$-$B_{30}$;

$B_1$

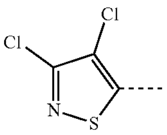

$B_2$

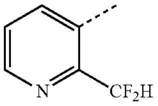

$B_3$

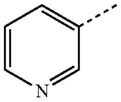

$B_4$

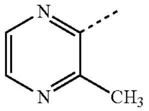

-continued $B_5$

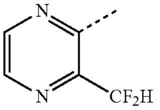

$B_6$

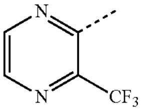

$B_{11}$

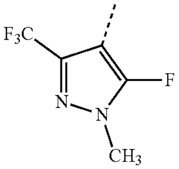

$B_{12}$

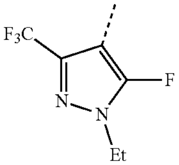

$B_{13}$

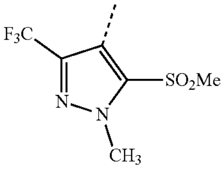

$B_{14}$

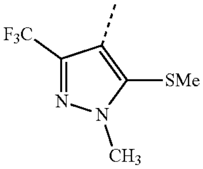

$B_{21}$

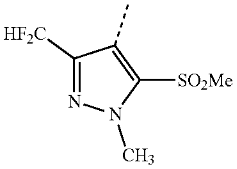

$B_{22}$

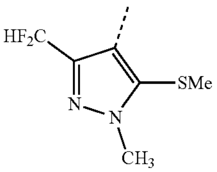

$B_{23}$

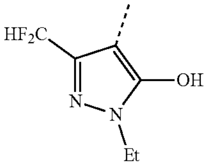

-continued $B_{24}$

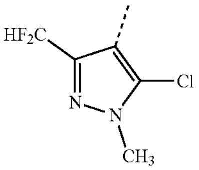

$B_{25}$

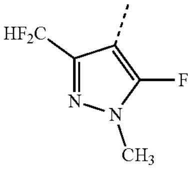

$B_{26}$

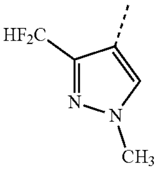

$B_{27}$

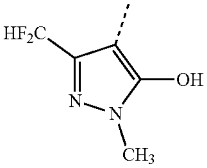

$B_{28}$

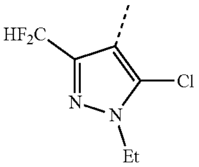

$B_{29}$

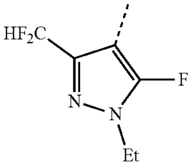

$B_{30}$

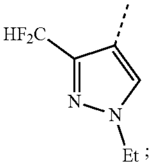

;

In the amide compound containing substituted acetophenone structural fragments of the present invention, a further preferred compound comprises: in the general formula I shown:

$R_1$ is selected from hydrogen, fluorine, chlorine, methyl, ethyl or isopropyl;

$R_2$ is selected from hydrogen, isopropyl, n-propyl, 2-butyl, 2-pentyl, cyclopropyl, cyclopentyl, cyclohexyl, trifluoromethyl or 2,2,2-trifluoroethyl;

$R_3$ is selected from hydrogen, methyl, ethyl or trifluoromethyl;

$R_4$ is selected from methyl, ethyl or trifluoromethyl;

B is selected from $B_1$, $B_2$, $B_{11}$, $B_{24}$, $B_{25}$, $B_{26}$ or $B_{27}$;

B1

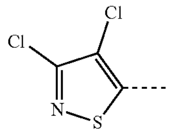

B2

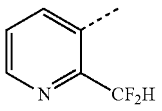

B11

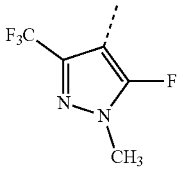

B24

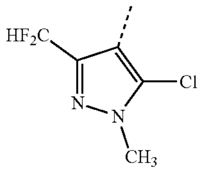

B25

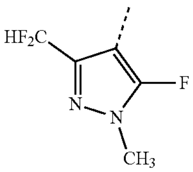

B26

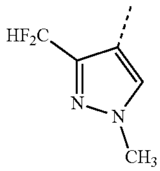

B27

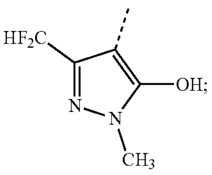

In the amide compound containing substituted acetophenone structural fragments of the present invention, a more further preferred compound comprises: in general formula I, $R_1$ is selected from hydrogen, chlorine or methyl;

$R_2$ is selected from isopropyl, 2-butyl, 2-pentyl, cyclopropyl or cyclopentyl;

$R_3$ is selected from hydrogen or methyl;

$R_4$ is selected from methyl or ethyl;

B is selected from $B_2$, $B_{11}$, $B_{24}$, $B_{25}$ or $B_{26}$;

B2

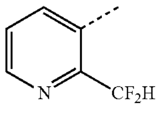

-continued

B11

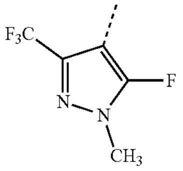

B24

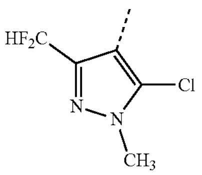

B25

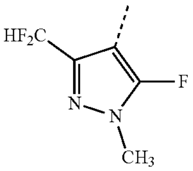

B26

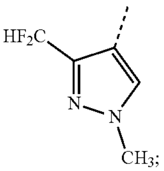

In the definitions of the compounds of the general formula I provided above, the terms used in the collection are generally defined as follows:

Halogen: fluorine, chlorine, bromine or iodine. Alkyl: linear or branched alkyl, such as methyl, ethyl, propyl, isopropyl, n-butyl or tert-butyl. Cycloalkyl: substituted or unsubstituted cyclic alkyl, such as cyclopropyl, cyclopentyl or cyclohexyl. Substituents such as methyl and halogen. Haloalkyl: linear or branched alkyl on which hydrogen atoms can be partially or fully replaced by the halogens, such as chloromethyl, dichloromethyl, trichloromethyl, fluoromethyl, difluoromethyl and trifluoromethyl. Haloalkoxy: linear or branched alkoxy on which hydrogens can be partially or fully replaced by halogen atoms, such as chloromethoxy, dichloromethoxy, trichloromethoxy, fluoromethoxy, difluoromethoxy, trifluoromethoxy, chlorofluoromethoxy and trifluoroethoxy.

Alkoxyalkyl: alkyl-O-alkyl-, such as $CH_3OCH_2$—. Haloalkoxyalkyl: hydrogen atoms on the alkyl of the alkoxyalkyl can be partially or fully replaced by halogen atoms, such as $ClCH_2CH_2OCH_2$— and $CF_3CH_2OCH_2$—. Alkoxycarbonylalkyl: alkoxycarbonyl-alkyl-, such as $CH_3OCOCH_2$—. Alkoxyalkoxy: such as $CH_3OCH_2O$—. Haloalkoxyalkoxy: hydrogen atoms on the alkoxy can be partially or fully replaced by halogen atoms, such as $CF_3OCH_2O$—. Alkylthio: linear or branched alkyl bonded to the structure through a sulfur atom. Haloalkylthio: linear or branched alkylthio, and hydrogen atoms on the alkyls may be partially or fully replaced by halogen atoms, for example, chloromethylthio, dichloromethylthio, trichloromethylthio, fluoromethylthio, difluoromethylthio, trifluoromethylthio and chlorofluoromethylthio. Alkylthioalkyl: alkyl-S-alkyl-, such as $CH_3SCH_2$—. Haloalkylthioalkyl: hydrogen atoms on the alkyl of the alkylthioalkyl can be partially or fully replaced by halogen atoms, such as $ClCH_2CH_2SCH_2$— and $CF_3CH_2SCH_2$—. Alkenyl: linear or branched alkene, such as vinyl, 1-propenyl, 2-propenyl and different butenyl, pentenyl and hexenyl isomers. Alkenyl also includes polyenes such as 1,2-propadienyl and 2,4-hexadienyl. Haloalkenyl: linear or branched alkene, and hydrogen atoms in the alkenyls may be partially or fully replaced by halogen atoms. Alkenyloxy: linear or branched alkene, bonded to the structure through an oxygen atom. Haloalkenyloxy: linear or branched alkenyloxy, and hydrogen atoms on the alkenyloxies may be partially or fully replaced by halogen atoms. Alkenylthio: linear or branched alkene, bonded to the structure through a sulfur atom, such as $CH_2$=$CHCH_2S$—. Alkenyloxycarbonyl: such as $CH_2$=$CHCH_2OCO$—, etc. Alkynyl: linear or branched alkyne, such as ethynyl, 1-propynyl, 2-propynyl and different butynyl, pentynyl and hexynyl isomers. Alkynyl also includes groups composed of multiple triple bonds, such as 2,5-hexadiynyl. Haloalkynyl: linear or branched alkyne, and hydrogen atoms on the alkynyls may be partially or fully replaced by halogen atoms. Alkynoxy: linear or branched alkyne, bonded to the structure through an oxygen atom. Haloalkynyloxy: linear or branched alkynyloxy, and hydrogen atoms on the alkynyloxies may be partially or fully replaced by halogen atoms. Cycloalkylalkyl: alkyl chain with a substituted or unsubstituted cyclic alkyl, such as cyclopropylmethyl, cyclohexylmethyl, etc. Halogen-substituted isothiazolyl: isothiazolyl substituted with one to two halogens, and the halogens may be the same or different, such as 3,4-dichloro-isothiazol-5-yl and 3,5-dibromo-isothiazol-4-yl.

The general or preferred group definitions or descriptions listed above may also be combined with each other as required, i.e., including combinations within ranges and preferred ranges. The definitions apply to final products and correspondingly apply to precursors and intermediates. In addition, some definitions may not apply.

The compound of the present invention is prepared according to the following method, and the reaction formulas are as follows. Each group in the formulas is defined as before unless otherwise stated:

The preparation of general formula compound I-1 can adopt the following method:

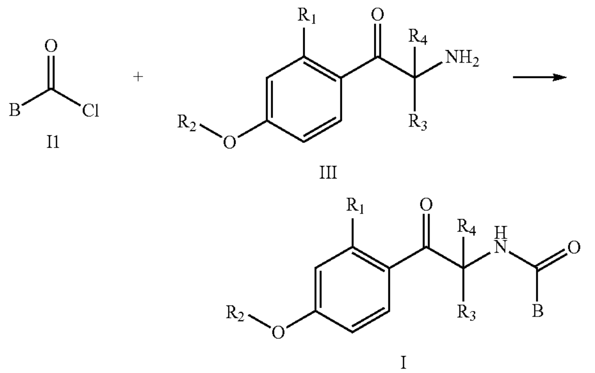

II III I

Or with reference to Reference Bioorganic & Medicinal Chemistry Letters, 13(3), 475-478; 2003 and WO2014184235 according to the following methods:

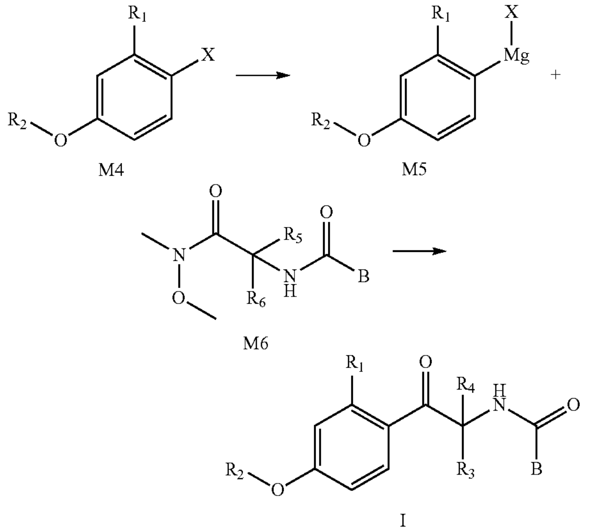

M4 M5 M6 I

The compound of general formula I is obtained through reaction of intermediates II and III in a suitable solvent under alkaline conditions.

A suitable alkali can be selected from, for example, potassium hydroxide, sodium hydroxide, sodium carbonate, potassium carbonate, sodium bicarbonate, triethylamine, pyridine, sodium methoxide, sodium ethoxide, sodium hydride, potassium tert-butoxide or sodium tert-butoxide.

The reaction is carried out in a suitable solvent. The suitable solvent can be selected from, for example, dichloromethane, trichloromethane, tetrahydrofuran, 1,4-dioxane, acetonitrile, toluene, xylene, benzene, N,N-dimethylformamide, N-methylpyrrolidone, dimethyl sulfoxide, acetone or butanone.

The reaction temperature can be between low temperature and the boiling point of the solvent, usually −10° C. to 100° C.

The reaction time is 30 minutes to 20 hours, usually 1-10 hours.

Part of the intermediate II is commercially available, and can also be prepared by known methods, for example, referring to the methods described in documents WO2016142918A1, WO2011061205A1, EP 569912, WO2015197530A2, Org. Process Res. Dev. 2017, 21, 3, 448-450.

The intermediate III is a key intermediate for preparing the compound of general formula I of the present invention, and is prepared by the following method:

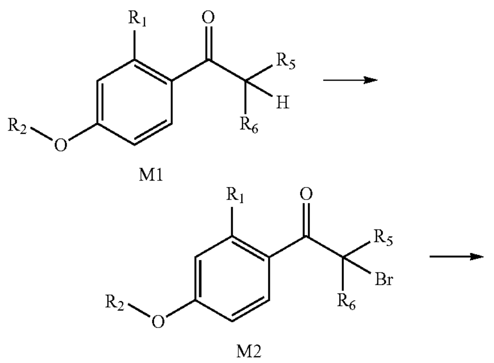

M1 M2

-continued

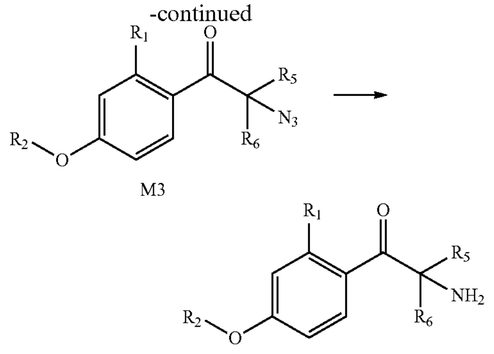

M3

III

Intermediate M1 and copper bromide react at suitable temperature, with ethyl acetate as a solvent for 30 minutes to 10 hours, usually 1-4 hours, to prepare intermediate M2. For the operation method of this step, refer to: Chinese Journal of Medicinal Chemistry, 12(6), 340-343; 2002; M2 and sodium azide react in dimethyl sulfoxide at suitable temperature for 30 minutes to 10 hours to prepare M3. For the operation method of this step, refer to: Zhang Shukang. Study on the synthesis process of succinate dehydrogenase inhibitor type fungicide Isofetamid [D]. Wuhan: Wuhan Institute of Technology, 2016. and WO2006016708A1. Finally, through the reduction of triphenylphosphine or zinc powder and ammonium chloride solution, III is prepared. For the operation method of this step, refer to WO2007069777A2 and Chemical Journal of Chinese Universities, 25(5), 866-869; 2004.

Although the compound of general formula I of the present invention and some compounds disclosed in the prior art also belong to amide compounds, there are still differences in structural characteristics. Moreover, because of the structural differences, the compound of the present invention has better fungal activity.

The compound of general formula I shows excellent activity against various germs in agriculture or other fields. Therefore, the technical solution of the present invention also includes the application of the compound of general formula I for preparing fungicides in agriculture or other fields.

The examples of diseases mentioned below are only intended to illustrate the present invention, but not to limit the present invention.

The compound of general formula I can be used to control the following diseases: Oomycetes diseases, such as downy mildew (cucumber downy mildew, rape downy mildew, soybean downy mildew, sugar beet downy mildew, sugarcane downy mildew, tobacco downy mildew, pea downy mildew, loofah downy mildew, wax gourd downy mildew, melon downy mildew, cabbage downy mildew, spinach downy mildew, radish downy mildew, grape downy mildew and onion downy mildew), Albugo candida (rape Albugo candida and cabbage Albugo candida), damping off (rape damping off, tobacco damping off, tomato damping off, pepper damping off, eggplant damping off, cucumber damping off and cotton seedling damping off), cotton rot (pepper cotton rot, loofah cotton rot and wax gourd cotton rot), blight (broad bean blight, cucumber blight, pumpkin blight, wax gourd blight, watermelon blight, melon blight, pepper blight, leek blight, garlic blight and cotton blight), late blight (potato late blight and tomato late blight); deuteromycete disease, such as wilt (sweet potato wilt, cotton wilt, sesame wilt, castor wilt, tomato wilt, kidney bean wilt, cucumber wilt, loofah wilt, pumpkin wilt, wax gourd wilt, watermelon wilt, melon wilt, pepper wilt, broad bean wilt, rapeseed wilt and soybean wilt), root rot (chili root rot, eggplant root rot, kidney bean root rot, cucumber root rot, bitter gourd root rot, cotton black root rot disease and broad bean root rot), wither (cotton seedling wither, sesame wither, pepper wither, cucumber wither and cabbage wither), anthrax (sorghum anthracnose, cotton anthracnose, kenaf anthracnose, jute anthracnose, flax anthracnose, tobacco anthracnose, mulberry anthracnose, pepper anthracnose, eggplant anthracnose, kidney bean anthracnose, cucumber anthracnose, bitter gourd anthracnose, zucchini anthracnose, winter melon anthracnose, watermelon anthracnose, muskmelon anthracnose and lychee anthracnose), verticillium wilt (cotton verticillium wilt, sunflower verticillium wilt, tomato verticillium wilt, pepper verticillium wilt and eggplant verticillium wilt), scab (zucchini scab, wax gourd scab and muskmelon scab), gray mold (cotton boll gray mold, kenaf gray mold, tomato gray mold, pepper gray mold, bean gray mold, celery gray mold, spinach gray mold and kiwifruit gray mold), brown spot (cotton brown spot, jute brown spot, beet brown spot, peanut brown spot, pepper brown spot, wax gourd brown spot, soybean brown spot, sunflower brown spot, pea brown spot and broad bean brown spot), black spot (flax false black spot, rapeseed black spot, sesameb lack spot, sunflower black spot, castor black spot, tomato black spot, pepper black spot, eggplant black spot, kidney bean black spot, cucumber black spot, celery black spot, carrot black rot, carrot black spot, apple black spot and peanut black spot), spot blight (tomato spot blight, pepper spot blight and celery spot blight), early blight (tomato early blight, pepper early blight, eggplant early blight, potato early blight and celery early blight), ring spot (soybean ring spot, sesame ring spot and kidney bean ring spot), leaf blight (sesame leaf blight, sunflower leaf blight, watermelon leaf blight and muskmelon leaf blight), stem base rot (tomato stem rot and kidney bean stem rot), and others (corn spot disease, kenaf lumbar fold disease, rice blast, chestnut black sheath disease, sugarcane eye spot disease, cotton boll aspergillosis, peanut crown rot, soybean stem blight, soybean black spot, melon large leaf spot, panut net spot disease, tea red leaf spot, pepper white spot disease, wax gourd leaf spot, celery black rot, spinach heart rot, kenaf leaf mildew, kenaf spot, jute stem spot, soybean purple spot, sesame leaf spot, castor grey spot, tea-brown leaf spot, eggplant brown spot disease, kidney bean red spot disease, bitter gourd white spot disease, watermelon spot, jute blight, sunflower rhizome rot, bean charcoal rot, soybean target spot, eggplant leaf spot, cucumber target spot, tomato leaf mildew, eggplant leaf mildew and broad bean red leaf spot); basidiomycete diseases such as rust (wheat stripe rust, wheat stem rust, wheat leaf rust, peanut rust, sunflower rust, sugarcane rust, leek rust, onion rust, chestnut rust and soybean rust), smut (corn head smut, corn smut, sorghum head smut, sorghum smut, sorghum solid smut, sorghum beam smut, chestnut smut, sugarcane smut and bean rust) and others (such as wheat sheath blight, rice sheath blight, etc.); ascomycete diseases such as powdery mildew (wheat powdery mildew, rape powdery mildew, sesame powdery mildew, sunflower powdery mildew, sugar beet powdery mildew, eggplant powdery mildew, pea powdery mildew, loofah powdery mildew, pumpkin powdery mildew, zucchini powdery mildew, wax gourd powdery mildew disease, melon powdery mildew, grape powdery mildew and broad bean powdery mildew), sclerotinia (flax sclerotinia, rape sclerotinia, soybean sclerotinia, peanut sclerotinia, tobacco sclerotinia, pepper sclerotinia, eggplant sclerotinia, bean sclerotinia, pea sclerotinia, cucumber sclerotinia, bitter gourd sclerotinia, wax gourd sclerotinia, watermelon sclerotinia and celery sclerotinia), sclerotinia (apple scab and pear scab), etc.

Due to the positive properties, the above compounds can be advantageously used to protect agriculturally and horticulturally important crops, livestock and breeding stock, as well as the environment frequented by humans, from germs.

To obtain an ideal effect, the use amount of the compound is changed due to various factors such as used compound, crop to be protected, types of pests, the degree of infestation, climatic conditions, administration methods and the adopted dosage forms.

The dosage of 10 g to 5 kg of compound per hectare can provide adequate control.

The present invention also includes a fungal composition using the compound shown by the general formula I as an active ingredient. The weight percentage of the active ingredient in the fungal composition is between 0.5% and 99%. The fungal composition also includes acceptable carriers in agriculture, forestry and hygiene.

The technical solution of the present invention also includes a method for controlling germs: applying the fungal composition of the present invention to the germs or growth media. A suitable effective amount usually selected is 10 g to 1000 g per hectare, and a preferred effective amount is 20 g to 500 g per hectare.

For certain applications, such as in agriculture, one or more other fungicides, insecticides, acaricides, herbicides, plant growth regulators or fertilizers can be added to the fungal composition of the present invention, thereby producing additional advantages and effects.

It should be clear that various changes and modifications can be made within the scope defined by the claims of the present invention.

DETAILED DESCRIPTION

The following specific embodiments are used to further illustrate the present invention, but the present invention is not limited to these examples (unless otherwise noted, all raw materials used are commercially available).

Synthesis Embodiment

Embodiment 1: preparation of intermediate α-amino-4-isopropoxy-2-methylphenyl isobutanone

1) Preparation of α-bromo-4-isopropoxy-2-methylphenyl isobutanone

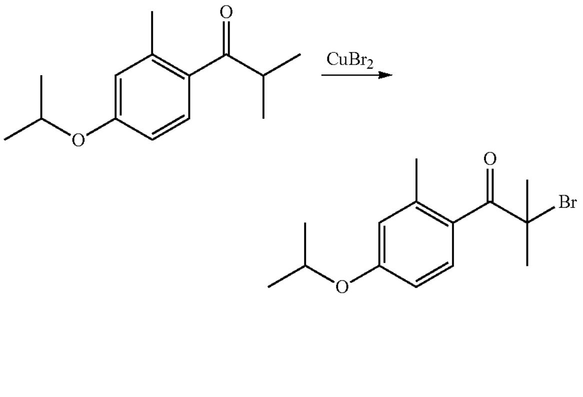

30 g (0.136 mol) of 4-isopropoxy-2-methylphenyl isobutanone and 50 g (0.224 mol) of copper bromide were put into a three-necked flask containing 250 ml of ethyl acetate, and heated to 70° C. to react for 5-18 hours. After the reaction was monitored by HPLC, the reaction solution was cooled to room temperature and filtered; and a filter cake was washed with ethyl acetate, washed with sodium bicarbonate solution, dried and then subjected to column chromatography to obtain 35 g of light yellow oil, with a yield of 85.9%.

2) Preparation of α-azido-4-isopropoxy-2-methylphenyl isobutanone

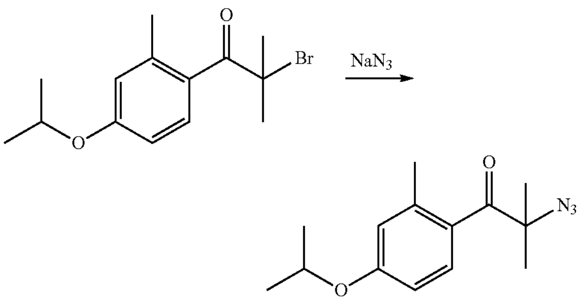

35 g (0.117 mol) of α-bromo-4-isopropoxy-2-methylphenyl isobutanone was put into a 500 ml three-necked flask, and heated to 50° C. by using 100 ml of dimethyl sulfoxide as a solvent; and 15.21 g (0.234 mol) of sodium azide was added in batches to react for 4-6 hours. After the reaction was monitored by HPLC, the reaction solution was poured into water after cooling, extracted with ethyl acetate for three times, washed with brine, dried, and then subjected to column chromatography to obtain 25 g of light yellow oil, with a yield of 81.8%.

3) Preparation of α-amino-4-isopropoxy-2-methylphenyl isobutanone

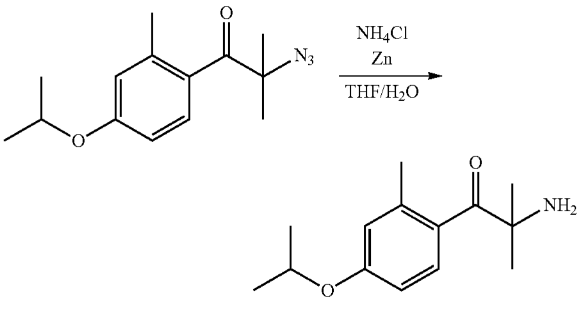

25 g (95.67 mmol) of α-azido-4-isopropoxy-2-methylphenyl isobutanone was put into a 500 ml three-necked flask; 450 ml of tetrahydrofuran was used as a solvent; 50 ml of water was added at 0-15° C.; 12.51 g (0.191 mol) of zinc powder was added; and 7 g (0.131 mol) of saturated ammonium chloride solution was added dropwise to react for 4-16 hours. After the reaction was monitored by HPLC, the reaction solution was filtered, washed twice with saturated brine, dried and then subjected to column chromatography to obtain 17 g of light yellow oil; and white solid or colorless crystals can be precipitated after storage for a long time, with a yield of 75.51%.

Embodiment 2: Preparation of Compound I-2

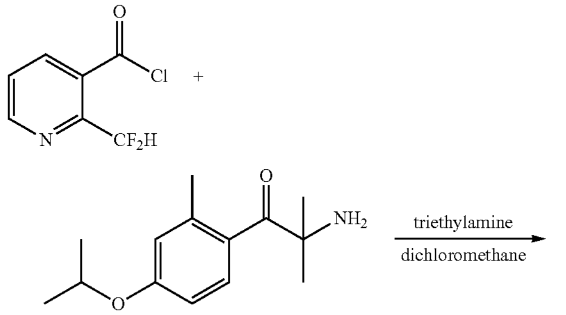

-continued

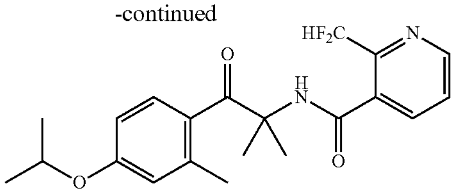

0.235 g (1 mmol) of α-amino-4-isopropoxy-2-methylphenyl isobutanone was added into 20 ml of dichloromethane, and 0.230 g (1.2 mmol, 1.2 eqiv) of 2-difluoromethylnicotinyl chloride was added dropwise under an ice bath. 0.121 g (1.2 mmol, 1.2 eqiv) of triethylamine was added dropwise, and the solution was naturally heated to room temperature to react for 2-6 hours. After the reaction was monitored by HPLC, after desolvation, the residues were subjected to column chromatography, with eluents of ethyl acetate and petroleum ether (boiling range of 60-90° C.), and a volume ratio of 0:100 to 20:80 for gradient elution to obtain 0.251 g of yellow solid, with a yield of 64.3%.

According to the preparation method of the compound of the general formula I described above and the specific process provided in the synthesis embodiments, other compounds shown by the general formula I can be obtained only by replacing the raw material materials (see Table 1).

TABLE 1

Structure and physical properties of some compounds of general formula I

| Compound No. | $R_1$ | $R_2$ | $R_3$ | $R_4$ | B | Appearance | Melting point (° C.) |
|---|---|---|---|---|---|---|---|
| I-1 | Me | i-Pr | Me | Me | $B_1$ | Yellow wax | |
| I-2 | Me | i-Pr | Me | Me | $B_2$ | Yellow solid | 96.9 |
| I-3 | Me | i-Pr | Me | Me | $B_3$ | Yellow solid | 125.5 |
| I-4 | Me | i-Pr | Me | Me | $B_4$ | | |
| I-5 | Me | i-Pr | Me | Me | $B_5$ | Yellow wax | |
| I-6 | Me | i-Pr | Me | Me | $B_6$ | | |
| I-7 | Me | i-Pr | Me | Me | $B_7$ | | |
| I-8 | Me | i-Pr | Me | Me | $B_8$ | | |
| I-9 | Me | i-Pr | Me | Me | $B_9$ | | |
| I-10 | Me | i-Pr | Me | Me | $B_{10}$ | | |
| I-11 | Me | i-Pr | Me | Me | $B_{11}$ | White solid | 118.1 |
| I-12 | Me | i-Pr | Me | Me | $B_{12}$ | | |
| I-13 | Me | i-Pr | Me | Me | $B_{13}$ | | |
| I-14 | Me | i-Pr | Me | Me | $B_{14}$ | | |
| I-15 | Me | i-Pr | Me | Me | $B_{15}$ | White solid | 146.6 |
| I-16 | Me | i-Pr | Me | Me | $B_{16}$ | White solid | 148.3 |
| I-17 | Me | i-Pr | Me | Me | $B_{17}$ | White solid | 139.3 |
| I-18 | Me | i-Pr | Me | Me | $B_{18}$ | White solid | 102.2 |
| I-19 | Me | i-Pr | Me | Me | $B_{19}$ | White solid | 108.4 |
| I-20 | Me | i-Pr | Me | Me | $B_{20}$ | | |
| I-21 | Me | i-Pr | Me | Me | $B_{21}$ | Colorless glass | |
| I-22 | Me | i-Pr | Me | Me | $B_{22}$ | Colorless glass | |
| I-23 | Me | i-Pr | Me | Me | $B_{23}$ | | |
| I-24 | Me | i-Pr | Me | Me | $B_{24}$ | White solid | 84.4 |
| I-25 | Me | i-Pr | Me | Me | $B_{25}$ | Yellow wax | |
| I-26 | Me | i-Pr | Me | Me | $B_{26}$ | White solid | 119.4 |
| I-27 | Me | i-Pr | Me | Me | $B_{27}$ | Yellow solid | 130.5 |
| I-28 | Me | i-Pr | Me | Me | $B_{28}$ | | |
| I-29 | Me | i-Pr | Me | Me | $B_{29}$ | | |
| I-30 | Me | i-Pr | Me | Me | $B_{30}$ | | |
| I-31 | Me | i-Pr | H | Me | $B_1$ | | |
| I-32 | Me | i-Pr | H | Me | $B_2$ | | |
| I-33 | Me | i-Pr | H | Me | $B_3$ | | |
| I-34 | Me | i-Pr | H | Me | $B_4$ | | |
| I-35 | Me | i-Pr | H | Me | $B_5$ | | |
| I-36 | Me | i-Pr | H | Me | $B_6$ | | |
| I-37 | Me | i-Pr | H | Me | $B_7$ | | |
| I-38 | Me | i-Pr | H | Me | $B_8$ | | |
| I-39 | Me | i-Pr | H | Me | $B_9$ | | |
| I-40 | Me | i-Pr | H | Me | $B_{10}$ | | |
| I-41 | Me | i-Pr | H | Me | $B_{11}$ | | |

TABLE 1-continued

Structure and physical properties of some compounds of general formula I

| Compound No. | $R_1$ | $R_2$ | $R_3$ | $R_4$ | B | Appearance | Melting point (° C.) |
|---|---|---|---|---|---|---|---|
| I-42 | Me | i-Pr | H | Me | $B_{12}$ | | |
| I-43 | Me | i-Pr | H | Me | $B_{13}$ | | |
| I-44 | Me | i-Pr | H | Me | $B_{14}$ | | |
| I-45 | Me | i-Pr | H | Me | $B_{15}$ | | |
| I-46 | Me | i-Pr | H | Me | $B_{16}$ | | |
| I-47 | Me | i-Pr | H | Me | $B_{17}$ | | |
| I-48 | Me | i-Pr | H | Me | $B_{18}$ | | |
| I-49 | Me | i-Pr | H | Me | $B_{19}$ | | |
| I-50 | Me | i-Pr | H | Me | $B_{20}$ | | |
| I-51 | Me | i-Pr | H | Me | $B_{21}$ | | |
| I-52 | Me | i-Pr | H | Me | $B_{22}$ | | |
| I-53 | Me | i-Pr | H | Me | $B_{23}$ | | |
| I-54 | Me | i-Pr | H | Me | $B_{24}$ | | |
| I-55 | Me | i-Pr | H | Me | $B_{25}$ | | |
| I-56 | Me | i-Pr | H | Me | $B_{26}$ | | |
| I-57 | Me | i-Pr | H | Me | $B_{27}$ | | |
| I-58 | Me | i-Pr | H | Me | $B_{28}$ | | |
| I-59 | Me | i-Pr | H | Me | $B_{29}$ | | |
| I-60 | Me | i-Pr | H | Me | $B_{30}$ | | |
| I-61 | H | i-Pr | Me | Me | $B_1$ | | |
| I-62 | H | i-Pr | Me | Me | $B_2$ | | |
| I-63 | H | i-Pr | Me | Me | $B_3$ | | |
| I-64 | H | i-Pr | Me | Me | $B_4$ | | |
| I-65 | H | i-Pr | Me | Me | $B_5$ | | |
| I-66 | H | i-Pr | Me | Me | $B_6$ | | |
| I-67 | H | i-Pr | Me | Me | $B_7$ | | |
| I-68 | H | i-Pr | Me | Me | $B_8$ | | |
| I-69 | H | i-Pr | Me | Me | $B_9$ | | |
| I-70 | H | i-Pr | Me | Me | $B_{10}$ | | |
| I-71 | H | i-Pr | Me | Me | $B_{11}$ | | |
| I-72 | H | i-Pr | Me | Me | $B_{12}$ | | |
| I-73 | H | i-Pr | Me | Me | $B_{13}$ | | |
| I-74 | H | i-Pr | Me | Me | $B_{14}$ | | |
| I-75 | H | i-Pr | Me | Me | $B_{15}$ | | |
| I-76 | H | i-Pr | Me | Me | $B_{16}$ | | |
| I-77 | H | i-Pr | Me | Me | $B_{17}$ | | |
| I-78 | H | i-Pr | Me | Me | $B_{18}$ | | |
| I-79 | H | i-Pr | Me | Me | $B_{19}$ | | |
| I-80 | H | i-Pr | Me | Me | $B_{20}$ | | |
| I-81 | H | i-Pr | Me | Me | $B_{21}$ | | |
| I-82 | H | i-Pr | Me | Me | $B_{22}$ | | |
| I-83 | H | i-Pr | Me | Me | $B_{23}$ | | |
| I-84 | H | i-Pr | Me | Me | $B_{24}$ | | |
| I-85 | H | i-Pr | Me | Me | $B_{25}$ | | |
| I-86 | H | i-Pr | Me | Me | $B_{26}$ | | |
| I-87 | H | i-Pr | Me | Me | $B_{27}$ | | |
| I-88 | H | i-Pr | Me | Me | $B_{28}$ | | |
| I-89 | H | i-Pr | Me | Me | $B_{29}$ | | |
| I-90 | H | i-Pr | Me | Me | $B_{30}$ | | |
| I-91 | Me | c-Pr | Me | Me | $B_1$ | | |
| I-92 | Me | c-Pr | Me | Me | $B_2$ | | |
| I-93 | Me | c-Pr | Me | Me | $B_{11}$ | | |
| I-94 | Me | c-Pr | Me | Me | $B_{24}$ | | |
| I-95 | Me | c-Pr | Me | Me | $B_{25}$ | | |
| I-96 | Me | c-Pr | Me | Me | $B_{26}$ | | |
| I-97 | Me | s-Bu | Me | Me | $B_1$ | | |
| I-98 | Me | s-Bu | Me | Me | $B_2$ | | |
| I-99 | Me | s-Bu | Me | Me | $B_{11}$ | | |
| I-100 | Me | s-Bu | Me | Me | $B_{24}$ | | |
| I-101 | Me | s-Bu | Me | Me | $B_{25}$ | | |
| I-102 | Me | s-Bu | Me | Me | $B_{26}$ | | |
| I-103 | Me | s-pentyl | Me | Me | $B_1$ | | |
| I-104 | Me | s-pentyl | Me | Me | $B_2$ | | |
| I-105 | Me | s-pentyl | Me | Me | $B_{11}$ | | |
| I-106 | Me | s-pentyl | Me | Me | $B_{24}$ | | |
| I-107 | Me | s-pentyl | Me | Me | $B_{25}$ | | |
| I-108 | Me | s-pentyl | Me | Me | $B_{26}$ | | |
| I-109 | Me | cyclopentyl | Me | Me | $B_1$ | | |
| I-110 | Me | cyclopentyl | Me | Me | $B_2$ | | |
| I-111 | Me | cyclopentyl | Me | Me | $B_{11}$ | | |
| I-112 | Me | cyclopentyl | Me | Me | $B_{24}$ | | |
| I-113 | Me | cyclopentyl | Me | Me | $B_{25}$ | | |
| I-114 | Me | cyclopentyl | Me | Me | $B_{26}$ | | |

TABLE 1-continued

Structure and physical properties of some compounds of general formula I

| Compound No. | $R_1$ | $R_2$ | $R_3$ | $R_4$ | B | Appearance | Melting point (° C.) |
|---|---|---|---|---|---|---|---|
| I-115 | Me | c-Pr | H | Me | $B_1$ | | |
| I-116 | Me | c-Pr | H | Me | $B_2$ | | |
| I-117 | Me | c-Pr | H | Me | $B_{11}$ | | |
| I-118 | Me | c-Pr | H | Me | $B_{24}$ | | |
| I-119 | Me | c-Pr | H | Me | $B_{25}$ | | |
| I-120 | Me | c-Pr | H | Me | $B_{26}$ | | |
| I-121 | Me | s-Bu | H | Me | $B_1$ | | |
| I-122 | Me | s-Bu | H | Me | $B_2$ | | |
| I-123 | Me | s-Bu | H | Me | $B_{11}$ | | |
| I-124 | Me | s-Bu | H | Me | $B_{24}$ | | |
| I-125 | Me | s-Bu | H | Me | $B_{25}$ | | |
| I-126 | Me | s-Bu | H | Me | $B_{26}$ | | |
| I-127 | Me | s-pentyl | H | Me | $B_1$ | | |
| I-128 | Me | s-pentyl | H | Me | $B_2$ | | |
| I-129 | Me | s-pentyl | H | Me | $B_{11}$ | | |
| I-130 | Me | s-pentyl | H | Me | $B_{24}$ | | |
| I-131 | Me | s-pentyl | H | Me | $B_{25}$ | | |
| I-132 | Me | s-pentyl | H | Me | $B_{26}$ | | |
| I-133 | Me | cyclopentyl | H | Me | $B_1$ | | |
| I-134 | Me | cyclopentyl | H | Me | $B_2$ | | |
| I-135 | Me | cyclopentyl | H | Me | $B_{11}$ | | |
| I-136 | Me | cyclopentyl | H | Me | $B_{24}$ | | |
| I-137 | Me | cyclopentyl | H | Me | $B_{25}$ | | |
| I-138 | Me | cyclopentyl | H | Me | $B_{26}$ | | |
| I-139 | Me | i-Pr | Me | Et | $B_1$ | | |
| I-140 | Me | i-Pr | Me | Et | $B_2$ | | |
| I-141 | Me | i-Pr | Me | Et | $B_{11}$ | | |
| I-142 | Me | i-Pr | Me | Et | $B_{24}$ | | |
| I-143 | Me | i-Pr | Me | Et | $B_{25}$ | | |
| I-144 | Me | i-Pr | Me | Et | $B_{26}$ | | |
| I-145 | Me | i-Pr | H | Et | $B_1$ | | |
| I-146 | Me | i-Pr | H | Et | $B_2$ | | |
| I-147 | Me | i-Pr | H | Et | $B_{11}$ | | |
| I-148 | Me | i-Pr | H | Et | $B_{24}$ | | |
| I-149 | Me | i-Pr | H | Et | $B_{25}$ | | |
| I-150 | Me | i-Pr | H | Et | $B_{26}$ | | |
| I-151 | H | i-Pr | H | Et | $B_1$ | | |
| I-152 | H | i-Pr | H | Et | $B_2$ | | |
| I-153 | H | i-Pr | H | Et | $B_{11}$ | | |
| I-154 | H | i-Pr | H | Et | $B_{24}$ | | |
| I-155 | H | i-P1 | H | Et | $B_{25}$ | | |
| I-156 | H | i-Pr | H | Et | $B_{26}$ | | |
| I-157 | H | i-Pr | H | Me | $B_1$ | | |
| I-158 | H | i-Pr | H | Me | $B_2$ | | |
| I-159 | H | i-Pr | H | Me | $B_{11}$ | | |
| I-160 | H | i-Pr | H | Me | $B_{24}$ | | |
| I-161 | H | i-Pr | H | Me | $B_2$ | | |
| I-162 | H | i-Pr | H | Me | $B_{26}$ | White paste | |
| I-163 | Cl | i-Pr | Me | Me | $B_1$ | | |
| I-164 | Cl | i-Pr | Me | Me | $B_2$ | | |
| I-165 | Cl | i-Pr | Me | Me | $B_{11}$ | | |
| I-166 | Cl | i-Pr | Me | Me | $B_{24}$ | | |
| I-167 | Cl | i-Pr | Me | Me | $B_{25}$ | | |
| I-168 | Cl | i-Pr | Me | Me | $B_{26}$ | | |

Other compounds of the present invention can be prepared with reference to the above embodiments.

The physical property data and nuclear magnetic data ($^1$HNMR, 600 MHz, internal standard TMS, ppm) of some compounds are as follows:

Compound I-1: $^1$H NMR (600 MHz, $CDCl_3$) δ 8.14 (s, 1H), 7.42 (d, J=8.6 Hz, 1H), 6.77 (d, J=2.4 Hz, 1H), 6.67 (dd, J=8.6, 2.5 Hz, 1H), 4.59 (hept, J=6.1 Hz, 1H), 2.33 (s, 3H), 1.82 (s, 6H), 1.34 (d, J=6.1 Hz, 6H).

Compound I-2: $^1$H NMR (600 MHz, $CDCl_3$) δ 8.70 (d, J=4.0 Hz, 1H), 7.67 (d, J=7.6 Hz, 1H), 7.47 (d, J=8.6 Hz, 1H), 7.40 (dd, J=7.6, 4.9 Hz, 1H), 6.97 (s, 1H), 6.79 (d, J=1.7 Hz, 1H), 6.75 (t, J=54.5 Hz, 1H), 6.65 (dd, J=8.6, 2.1 Hz, 1H), 4.73-4.47 (m, 1H), 2.38 (s, 3H), 1.78 (s, 6H), 1.34 (d, J=6.0 Hz, 6H).

Compound I-3: $^1$H NMR (600 MHz, $CDCl_3$) δ 8.96 (d, J=1.8 Hz, 1H), 8.71 (dd, J=4.8, 1.5 Hz, 1H), 8.04 (dt, J=7.9, 1.9 Hz, 1H), 7.48 (d, J=8.6 Hz, 1H), 7.38-7.31 (m, 2H), 6.76 (d, J=2.4 Hz, 1H), 6.65 (dd, J=8.6, 2.5 Hz, 1H), 4.57 (hept, J=6.1 Hz, 1H), 2.36 (s, 3H), 1.81 (s, 6H), 1.33 (d, J=6.1 Hz, 6H).

Compound I-5: $^1$H NMR (600 MHz, $CDCl_3$) δ 8.86 (d, J=2.3 Hz, 1H), 8.79 (s, 1H), 8.68 (d, J=2.2 Hz, 1H), 7.75 (t, J=54.2 Hz, 1H), 7.46 (d, J=8.6 Hz, 1H), 6.75 (d, J=2.3 Hz, 1H), 6.59 (dd, J=8.6, 2.5 Hz, 1H), 4.59-4.52 (m, 1H), 2.38 (s, 3H), 1.80 (s, 6H), 1.31 (d, J=6.1 Hz, 6H).

Compound I-11: $^1$H NMR (600 MHz, $CDCl_3$) δ 7.43 (d, J=8.6 Hz, 1H), 7.02 (s, 1H), 6.75 (d, J=2.2 Hz, 1H), 6.64 (dd, J=8.6, 2.4 Hz, 1H), 4.66-4.48 (m, 1H), 3.81 (s, 3H), 2.33 (s, 3H), 1.76 (s, 6H), 1.33 (d, J=6.1 Hz, 6H).

Compound I-15: $^1$H NMR (600 MHz, $CDCl_3$) δ 7.67 (s, 1H), 7.44 (d, J=8.6 Hz, 1H), 6.77 (s, 1H), 6.75 (d, J=2.3 Hz, 1H), 6.64 (dd, J=8.6, 2.4 Hz, 1H), 4.57 (hept, J=6.0 Hz, 1H), 3.82 (s, 3H), 2.44 (s, 3H), 2.33 (s, 3H), 1.76 (s, 6H), 1.33 (d, J=6.1 Hz, 6H).

Compound I-16: $^1$H NMR (600 MHz, $CDCl_3$) δ 7.44 (d, J=8.6 Hz, 1H), 6.91 (s, 1H), 6.75 (d, J=2.3 Hz, 1H), 6.62 (dd, J=8.6, 2.4 Hz, 1H), 6.28 (s, 1H), 4.56 (hept, J=6.0 Hz, 1H), 4.34 (q, J=7.2 Hz, 2H), 2.36 (s, 3H), 2.26 (s, 3H), 1.76 (s, 6H), 1.33 (d, J=6.1 Hz, 6H), 1.28 (t, J=7.2 Hz, 3H).

Compound I-17: $^1$H NMR (600 MHz, $CDCl_3$) δ 7.54 (d, J=8.6 Hz, 1H), 7.50 (s, 1H), 6.72 (d, J=2.4 Hz, 1H), 6.59 (dd, J=8.6, 2.5 Hz, 1H), 6.43 (s, 1H), 4.55 (hept, J=6.1 Hz, 1H), 3.78 (s, 3H), 2.39 (s, 3H), 2.25 (s, 3H), 1.73 (s, 6H), 1.31 (d, J=6.1 Hz, 6H).

Compound I-18: $^1$H NMR (600 MHz, $CDCl_3$) δ 7.55 (d, J=8.6 Hz, 1H), 7.51 (s, 1H), 6.72 (d, J=2.1, 1H), 6.59 (dd, J=8.6, 2.0 Hz, 1H), 6.42 (s, 1H), 4.55 (hept, J=5.9 Hz, 1H), 4.07 (q, J=7.3 Hz, 2H), 2.39 (s, 3H), 2.26 (s, 3H), 1.73 (s, 6H), 1.42 (t, J=7.3 Hz, 3H), 1.31 (d, J=6.0 Hz, 6H).

Compound I-19: $^1$H NMR (600 MHz, $CDCl_3$) δ 7.42 (d, J=8.6 Hz, 1H), 7.06 (s, 1H), 6.77 (d, J=2.4 Hz, 1H), 6.67 (dd, J=8.6, 2.5 Hz, 1H), 4.58 (hept, J=6.0 Hz, 1H), 2.61 (s, 3H), 2.33 (s, 3H), 1.78 (s, 6H), 1.34 (d, J=6.1 Hz, 6H).

Compound I-21: $^1$H NMR (600 MHz, $CDCl_3$) δ 7.54 (s, 1H), 7.50 (d, J=8.6 Hz, 1H), 6.78 (t, J=53.7 Hz, 1H), 6.75 (d, J=2.3 Hz, 1H), 6.65 (dd, J=8.5, 2.3 Hz, 1H), 4.57 (hept, J=6.1 Hz, 1H), 4.22 (s, 3H), 3.39 (s, 3H), 2.35 (s, 4H), 1.73 (s, 6H), 1.33 (d, J=6.1 Hz, 6H).

Compound I-22: $^1$H NMR (600 MHz, $CDCl_3$) δ 8.19 (s, 1H), 7.47 (d, J=8.6 Hz, 1H), 7.13 (t, J=54.2 Hz, 1H), 6.74 (d, J=2.3 Hz, 1H), 6.61 (dd, J=8.6, 2.5 Hz, 1H), 4.56 (hept, J=6.0 Hz, 1H), 4.02 (s, 3H), 2.41 (s, 3H), 2.36 (s, 3H), 1.76 (s, 6H), 1.32 (d, J=6.1 Hz, 6H). MS: $[M+1]^+$ found 440.0, Cal 440.18; $[M+Na]^+$ found 461.9, Cal 462.16.

Compound I-24: $^1$H NMR (600 MHz, $CDCl_3$) δ 7.46 (d, J=8.6 Hz, 1H), 6.99 (t, J=54.0 Hz, 1H), 6.75 (d, J=2.3 Hz, 1H), 6.63 (dd, J=8.6, 2.4 Hz, 1H), 4.60-4.53 (m, 1H), 3.89 (s, 3H), 2.35 (s, 3H), 1.76 (s, 6H), 1.33 (d, J=6.1 Hz, 6H).

Compound I-25: $^1$H NMR (600 MHz, $CDCl_3$) δ 7.45 (d, J=8.6 Hz, 1H), 7.02 (s, 1H), 6.95 (t, J=53.9 Hz, 1H), 6.74 (d, J=2.2 Hz, 1H), 6.63 (dd, J=8.6, 2.4 Hz, 1H), 4.60-4.54 (m, 1H), 3.80 (s, 3H), 2.34 (s, 3H), 1.74 (s, 6H), 1.33 (d, J=6.0 Hz, 6H).

Compound I-26: $^1$H NMR (600 MHz, $CDCl_3$) δ 7.77 (s, 1H), 7.55 (d, J=8.6 Hz, 1H), 7.05 (s, 1H), 6.84 (t, J=54.2 Hz, 1H), 6.72 (d, J=2.4 Hz, 1H), 6.59 (dd, J=8.6, 2.5 Hz, 1H), 4.55 (hept, J=6.0 Hz, 1H), 3.86 (s, 3H), 2.39 (s, 3H), 1.72 (s, 6H), 1.31 (d, J=6.1 Hz, 6H).

Compound I-27: $^1$H NMR (600 MHz, $CDCl_3$) δ 10.72 (s, 1H), 7.70 (s, 1H), 7.25 (d, J=8.8 Hz, 1H), 6.75 (d, J=2.0 Hz, 1H), 6.68 (dd, J=8.6, 2.3 Hz, 1H), 6.41 (t, J=54.2 Hz, 1H), 4.62-4.51 (m, 1H), 3.46 (s, 3H), 2.28 (s, 3H), 1.71 (s, 6H), 1.33 (d, J=6.0 Hz, 6H).

Compound I-162: $^1$H NMR (600 MHz, $CDCl_3$) δ 7.85 (s, 1H), 7.27 (d, J=8.9 Hz, 2H), 6.99 (t, J=54.2 Hz, 1H), 6.96 (d, J=8.7 Hz, 2H), 4.92 (p, J=6.6 Hz, 1H), 4.61-4.55 (m, 1H), 3.94 (s, 3H), 1.36 (dd, J=6.0, 1.1 Hz, 6H), 1.29 (d, J=6.7 Hz, 6H).

Embodiments of Determination of Biological Activity

The compounds of the present invention show good activity against various germs in the agricultural field.

Embodiment 3: Determination of Fungal Activity

The test of in vivo protection effect is conducted on various fungal diseases of plants through samples of the compounds of the present invention. The determination results of the fungal activity are shown in the following embodiments.

(1) Determination of In Vivo Protection Activity

The determination method is as follows: the to-be-determined sample of the compound of general formula I obtained above was dissolved with a small amount of solvent (the type of the solvent is, for example, acetone, methanol, DMF, etc., and is selected according to the dissolving ability to the sample; and the volume ratio of the solvent amount to the liquid spray amount is equal to or less than 0.05) by a live pot determination method, and diluted with water containing 0.1% Tween 80 to prepare to-be-determined liquid with required concentration. On a crop sprayer, the to-be-determined liquid was sprayed onto disease host plants (the host plants are standard potted seedlings cultivated in a greenhouse), and the disease was inoculated after 24 hours. According to the characteristics of the disease, the diseased plants that need to be cultivated under temperature control and moisturizing were inoculated and then placed in an artificial climate chamber for cultivation. After the disease completes infection, the disease was transferred into the greenhouse for cultivation, and the diseased plants that do not need moisturizing cultivation were directly inoculated and cultivated in the greenhouse. After full onset through control (usually one week), the disease prevention effect of the compound was evaluated.

The determination results of in vivo protection activity for some compounds are as follows:

In vivo protection activity against cucumber downy mildew:

At a dose of 400 ppm, compounds I-1, I-5, I-19, I-23 and I-25 have more than 80% control effects on cucumber downy mildew, and compounds CK1, CK2, CK3 and CK4 have 0 control effects on cucumber downy mildew.

In vivo protection activity against wheat powdery mildew:

At a dose of 100 ppm, compounds I-2 and I-25 have more than 90% control effects on wheat powdery mildew, and compounds CK1, CK2, CK3 and CK4 have control effects of 85%, 85%, 85% and 75% on wheat powdery mildew at a dose of 400 ppm.

In vivo protection activity against corn rust:

At a dose of 400 ppm, compounds I-21, I-26 and I-27 have more than 80% control effects on corn rust, and compounds CK1, CK2, CK3 and CK4 have 0 control effects on corn rust.

In vivo protection activity against cucumber anthracnose:

At a dose of 400 ppm, compounds I-1 and I-26 have control effects of 60% and 40% on cucumber anthracnose, and compounds CK1, CK2, CK3 and CK4 have 0 control effects on cucumber anthracnose.

In vivo protection activity against cucumber botrytis:

At a dose of 200 ppm, compound I-11 has more than 80% control effect on cucumber botrytis, and compounds CK1, CK2, CK3 and CK4 have control effects of 0, 0, 60% and 25% on cucumber botrytis.

In vivo protection activity against tomato botrytis:

At a dose of 100 ppm, compounds I-5, I-15, I-19, I-24 and I-25 have more than 80% control effects on tomato botrytis, and compounds CK2, CK3 and CK4 have control effects of 20%, 35% and 0 on tomato botrytis.

According to the above method, some compounds of the present invention and known compounds CK1 (self-made, No. I-20 in patent WO2007069777), CK2 (self-made, No. I-84 in patent WO2007069777), CK3 (self-made, No. I-6 in patent JP 2007210924) and CK4 (self-made, No. I-183 in patent JP 2007210924) were selected for conducting parallel determination of the activity of controlling cucumber downy mildew. Test results are shown in Table 2.

$^1$H NMR (600 MHz, $CDCl_3$) data and physicochemical data of the above obtained compounds CK1-CK4 are as follows:

CK1: $^1$H NMR (600 MHz, $CDCl_3$) δ 8.73 (d, J=3.9 Hz, 1H), 7.55 (d, J=7.5 Hz, 1H), 7.48 (dd, J=7.4, 4.9 Hz, 1H), 7.45 (d, J=8.5 Hz, 1H), 6.84 (s, 1H), 6.79 (s, 1H), 6.68 (dd, J=1.4 Hz, J=8.3 Hz, 1H), 4.64-4.57 (m, 1H), 2.36 (s, 3H), 1.80 (s, 6H), 1.35 (d, J=6.0 Hz, 6H). White solid, m.p. 88.6° C.

CK2: $^1$H NMR (600 MHz, $CDCl_3$) δ 8.48-8.31 (m, 1H), 7.79-7.77 (m, 1H), 7.50 (d, J=8.6 Hz, 1H), 7.29-7.25 (m, 2H), 6.77 (d, J=2.3 Hz, 1H), 6.64 (dd, J=8.6, 2.4 Hz, 1H), 4.62-4.55 (m, 1H), 2.38 (s, 3H), 1.81 (s, 6H), 1.34 (d, J=6.1 Hz, 6H). White solid, m.p. 124.3° C.

CK3: $^1$H NMR (600 MHz, $CDCl_3$) δ 7.81 (s, 1H), 7.48 (d, J=8.6 Hz, 1H), 6.87 (s, 1H), 6.74 (d, J=2.1 Hz, 1H), 6.61 (dd, J=8.6, 2.3 Hz, 1H), 4.62-4.50 (m, 1H), 3.92 (s, 3H), 2.36 (s, 3H), 1.73 (s, 6H), 1.32 (d, J=6.0 Hz, 6H). White solid, m.p. 137.4° C.

CK4: $^1$H NMR (600 MHz, $CDCl_3$) δ 7.43 (d, J=8.6 Hz, 1H), 7.05 (s, 1H), 6.75 (d, J=2.4 Hz, 1H), 6.64 (dd, J=8.6, 2.5 Hz, 1H), 4.57 (hept, J=6.3 Hz, 1H), 3.90 (s, 3H), 2.34 (s, 3H), 1.77 (s, 6H), 1.33 (d, J=6.1 Hz, 6H). White solid, m.p. 119.0° C.

TABLE 2

Comparison of control effects of some compounds of the present invention and known compounds on cucumber downy mildew

| Compound | Cucumber downy mildew 400 ppm |
|---|---|
| I-1 | 80 |
| I-2 | 40 |
| I-3 | 40 |
| I-5 | 85 |
| I-16 | 50 |
| I-18 | 40 |
| I-19 | 85 |
| I-21 | 40 |
| I-22 | 85 |
| I-25 | 85 |
| CK1 | 0 |
| CK2 | 0 |
| CK3 | 0 |
| CK4 | 0 |

According to the above method, some compounds of the present invention and known compounds were selected for conducting parallel determination of the activity of controlling wheat powdery mildew. Test results are shown in Table 3.

TABLE 3

Comparison of control effects of some compounds of the present invention and known compounds on wheat powdery mildew

| | Wheat powdery mildew | |
|---|---|---|
| Compound | 400 ppm | 100 ppm |
| I-1 | 98 | 70 |
| I-2 | 100 | 100 |
| I-25 | 100 | 90 |
| I-27 | 100 | 60 |
| I-162 | 100 | 20 |
| CK1 | 85 | — |
| CK2 | 85 | — |
| CK3 | 85 | — |
| CK4 | 75 | — |

Note:
"—" represents no test.

According to the above method, some compounds of the present invention and known compounds were selected for conducting parallel determination of the activity of controlling corn rust. Test results are shown in Table 4.

TABLE 4

Comparison of control effects of some compounds of the present invention and known compounds on corn rust

| Compound | Corn rust 400 ppm |
|---|---|
| I-1 | 60 |
| I-25 | 85 |
| I-26 | 100 |
| I-27 | 85 |
| I-162 | 30 |
| CK1 | 0 |
| CK2 | 0 |
| CK3 | 0 |
| CK4 | 0 |

According to the above method, some compounds of the present invention and known compounds were selected for conducting parallel determination of the activity of controlling cucumber botrytis. Test results are shown in Table 5.

TABLE 5

Comparison of control effects of some compounds of the present invention and known compounds on cucumber botrytis

| Compound | Control effects on cucumber botrytis (%) 200 ppm |
|---|---|
| I-11 | 80 |
| CK1 | 0 |
| CK2 | 0 |
| CK4 | 25 |

According to the above method, some compounds of the present invention and known compounds were selected for conducting parallel determination of the activity of controlling tomato botrytis. Test results are shown in Table 6.

TABLE 6

| Comparison of control effects of some compounds of the present invention and known compounds on tomato botrytis | | |
|---|---|---|
| | Control effects on tomato botrytis (%) | |
| Compound | 100 ppm | 25 ppm |
| I-5 | 80 | — |
| I-15 | 85 | 60 |
| I-19 | 80 | 60 |
| I-24 | 85 | 60 |
| I-25 | 100 | 98 |
| CK2 | 20 | 0 |
| CK3 | 35 | 20 |
| CK4 | 0 | 0 |

Note:
"—" represents no test.

The invention claimed is:

1. An amide compound of general formula I:

I

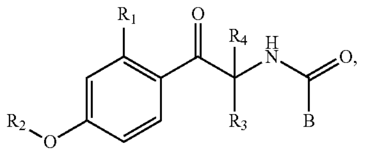

wherein:

$R_1$ is halogen or $C_1$-$C_4$ alkyl;

$R_2$ is $C_3$-$C_6$ cycloalkyl or halogenated $C_1$-$C_4$ alkyl;

$R_3$ is halogenated $C_1$-$C_4$ alkyl;

$R_4$ is $C_1$-$C_4$ alkyl or halogenated $C_1$-$C_4$ alkyl; and

B is selected from the group consisting of $B_1$, $B_{11}$ to $B_{14}$, and $B_{21}$ to $B_{30}$:

$B_1$

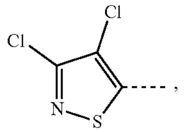

$B_{11}$

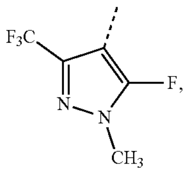

$B_{12}$

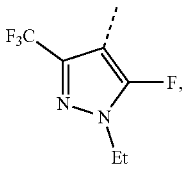

$B_{13}$

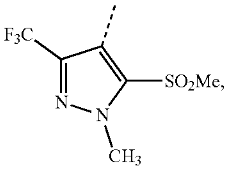

-continued $B_{14}$

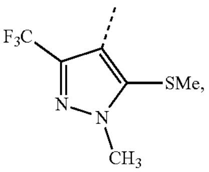

$B_{21}$

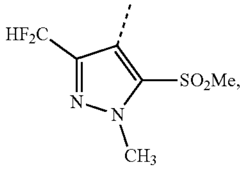

$B_{22}$

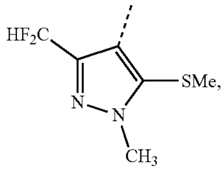

$B_{23}$

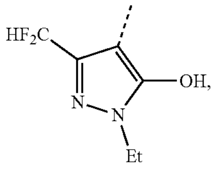

$B_{24}$

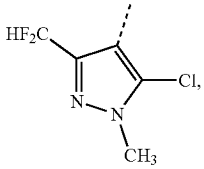

$B_{25}$

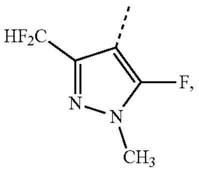

$B_{26}$

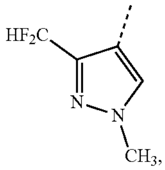

$B_{27}$

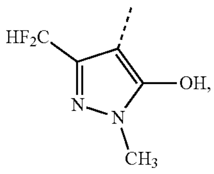

-continued

B28

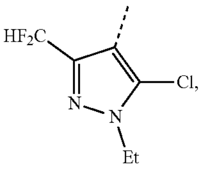

B29

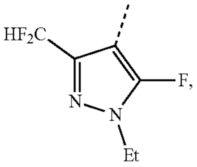

and

B30

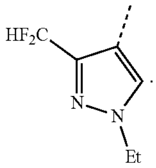

2. The amide compound according to claim 1, wherein:
$R_1$ is selected from the group consisting of fluorine, chlorine, methyl, ethyl, and isopropyl;
$R_2$ is selected from the group consisting of cyclopropyl, cyclopentyl, cyclohexyl, trifluoromethyl or 2,2,2-trifluoroethyl;
$R_3$ is trifluoromethyl;
$R_4$ is methyl, ethyl or trifluoromethyl; and
B is selected from the group consisting of $B_1$, $B_{11}$, $B_{24}$, $B_{25}$, $B_{26}$, and $B_{27}$:

$B_1$

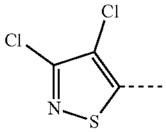

$B_{11}$

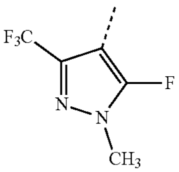

-continued

B24

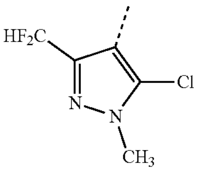

B25

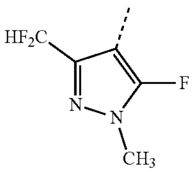

B26

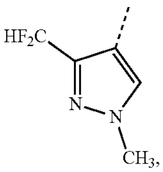

and

B27

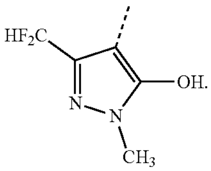

3. A fungicidal composition, comprising the compound of the general formula I according to claim 1 as an active ingredient and an acceptable carrier in agriculture, forestry or hygiene; and the weight percentage of the compound of the general formula I as the active ingredient in the composition is 1-99%.

4. A method for controlling a plant fungal disease, comprising applying the fungicidal composition of claim 3 to a growth medium, wherein a dosage of the composition is 10 g to 1000 g per hectare.

5. The method according to claim 4, wherein the fungal disease is selected from the group consisting of cucumber downy mildew, wheat powdery mildew, corn rust, cucumber anthracnose, cucumber botrytis, and tomato botrytis.

* * * * *